(12) United States Patent
Jain et al.

(10) Patent No.: US 7,956,067 B2
(45) Date of Patent: Jun. 7, 2011

(54) **COMPOSITION COMPRISING AT LEAST ONE HIGHER ALIPHATIC ALCOHOL AND AN EXTRACT OF *GRIFFONIA SIMPLICIFOLIA***

(75) Inventors: Rajesh Jain, New Delhi (IN); Kour Chand Jindal, New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 255 days.

(21) Appl. No.: 12/299,317

(22) PCT Filed: May 9, 2007

(86) PCT No.: PCT/IN2007/000188
§ 371 (c)(1),
(2), (4) Date: Nov. 3, 2008

(87) PCT Pub. No.: WO2007/132479
PCT Pub. Date: Nov. 22, 2007

(65) Prior Publication Data
US 2009/0258896 A1    Oct. 15, 2009

(30) Foreign Application Priority Data

May 11, 2006  (IN) .......................... 1175/DEL/2006

(51) Int. Cl.
| | | |
|---|---|---|
| *A61K 31/44* | (2006.01) | |
| *A61K 31/40* | (2006.01) | |
| *A61K 36/00* | (2006.01) | |
| *A61K 36/82* | (2006.01) | |

(52) U.S. Cl. ......... 514/299; 514/419; 424/725; 424/729
(58) Field of Classification Search .................. 514/299, 514/419; 424/725, 729
See application file for complete search history.

(56) References Cited

U.S. PATENT DOCUMENTS

2003/0162725 A1 * 8/2003 Riker et al. ..................... 514/19
2005/0124703 A1 * 6/2005 Jia et al. ........................ 514/724
* cited by examiner

*Primary Examiner* — Raymond J Henley, III
(74) *Attorney, Agent, or Firm* — Ladas & Parry LLP

(57) ABSTRACT

Novel compositions comprising a combination of at least one higher primary aliphatic alcohol preferably selected from those having 18 to 40 carbon atoms or mixtures thereof, at least one source of 5-hydroxytryptophan (5-HTP) optionally additionally comprising a source of caffeine and/or catechin-polyphenol and/or epigallocatechin gallate as active agents, either alone or in combination with other active agent(s), optionally with one or more excipient(s) are provided. Particularly, the invention relates to compositions and process for preparation of such compositions and method of use thereof for the management of obesity and associated disorders.

18 Claims, No Drawings

US 7,956,067 B2

COMPOSITION COMPRISING AT LEAST ONE HIGHER ALIPHATIC ALCOHOL AND AN EXTRACT OF *GRIFFONIA SIMPLICIFOLIA*

FIELD OF THE INVENTION

The present invention provides novel compositions comprising a combination of at least one higher primary aliphatic alcohol preferably selected from those having 18 to 40 carbon atoms or mixtures thereof, at least one source of 5-hydroxytryptophan (5-HTP) optionally additionally comprising a source of caffeine and/or catechin-polyphenol and/or epigallocatechin gallate as active agents, either alone or in combination with other active agent(s), optionally with one or more excipient(s). Particularly, the invention relates to compositions and process for preparation of such compositions method of use thereof for the management of obesity and associated disorders. The compositions of the present invention are useful as a pharmaceutical or as a dietary supplement.

BACKGROUND OF THE INVENTION

The therapeutic objective as regards obesity is well defined; it is a matter either of allowing the individual to lose a significant amount of weight, or of helping the individual to maintain a weight level, which is as low as desired. Several types of approaches have been envisaged to date. The prevalence of obesity in adults, children and adolescents has increased rapidly over the past 30 years in the United States and globally, and continues to rise. Obesity is classically defined based on the percentage of body fat or, more recently, the body mass index (BMI), also called Quetlet index (National Task Force on the Prevention and Treatment of Obesity, Arch. Intern. Med., 160: 898-904 (2000); Khaodhiar, L. et al., Clin. Cornerstone, 2: 17-31 (1999)). The BMI is defined as the ratio of weight (kg) divided by height (in meters) squared.

Overweight and obesity are associated with increasing the risk of developing many chronic diseases of aging seen in the U.S. (Must, A. et al., JAMA, 282: 1523-9 (1999)). The key to reducing the severity of the diseases is to lose weight effectively. Although about 30 to 40% claim to be trying to lose weight or maintain lost weight, current therapies appear not to be working. Besides dietary manipulation, pharmacological management and in extreme cases, surgery, are sanctioned adjunctive therapies to treat overweight and obese patients (Expert Panel, National Institute of Health, Heart, Lung, and Blood Institute, 1-42 (June 1998); Bray, G. A., Contemporary Diagnosis and Management of Obesity, 246-273 (1998)). Drugs have side effects, and surgery, although effective, is a drastic measure and reserved for morbidly obese. Nutritional approaches are directed toward reducing the supply of energy in the form of foods. This can be achieved either by drastically reducing the energy supplies or by replacing high-energy nutrients with others, which are lower in energy such as indigestible substitute fats, structured triglycerides that are difficult to assimilate or dietary fibers that cannot be assimilated.

5-HTP (5-Hydroxytryptophan) is a direct precursor of serotonin. 5-HTP is a natural compound isolated from the seeds of an African plant called *Griffonia simplicifolia*, grown mostly in Ghana and the Ivory Coast. It can also be made synthetically in the laboratory. Its toxicity is extremely low as noted by lethal dose (LD) studies. Studies conducted in the rat and mice have demonstrated that the $LD_{50}$ is negligible as compared to therapeutic doses: $LD_{50}$ per os and i.p. in the mouse 2500 mg/kg and 1400 mg/kg respectively. However, synthetically produced 5-HTP has been associated with a cluster of symptoms called eosinophilia-myalgia syndrome (EMS). EMS is a serious systemic illness characterized by elevations of certain white blood cells and severe muscle pain. In 1989 there was an epidemic outbreak of EMS, triggered by the consumption of synthetically prepared L-tryptophan produced by a fermentation process. More than 1,500 cases including at least 37 deaths were reported to the CDC as of February, 2001. 5-HTP isolated from the seeds of *Griffonia simplicifolia* does not require the use of a fermentation process and is a safer product.

Policosanol is a mixture of primary aliphatic alcohols isolated from plant waxes such as sugarcane. The aliphatic alcohol of the mixture is a $CH_3—(CH_2)_n—CH_2OH$ alcohol with chain length varying from 24 to 39 carbon atoms. Typical aliphatic alcohols of the mixture are octacosanol, hexacosanol, heptacosanol, triacontanol and dotriacontanol. Policosanol has been shown to lower cholesterol in animal models, healthy volunteers, and patients with type II hypercholesterolemia. Therefore, it is useful in the dyslipidemia associated with type 2 diabetes mellitus.

Green tea has long been known to have an effect on body weight and energy expenditure. Epigallocatechin gallate (abbreviated herein as EGCG) is a naturally occurring substance found chiefly in green tea and its extracts. EGCG is ideal as a weight loss agent because of its lack of toxicity or apparent side effects. EGCG and related catechins occur naturally in several types of plants, including tea, and thus have a long history of safety in that form. Recently, the anorectic effects of green tea have been attributed to polyphenols, especially the most abundant one-EGCG (Dulloo A G, et al. Am J Clin Nutr 1999; 70:1040-5). The thermogenesis effect of EGCG has also been shown to be dependent on the sympathetically released norepinephrine (NE) in the activation of peripheral thermogenesis (Dulloo A G. et al. Int J Obes Relat Metab Disord 2000; 24:252-8). These studies indicate that it is not EGCG alone, but the combination of EGCG and caffeine via their interaction with sympathetically released NE that confers green tea with its ability to enhance thermogenesis. The mechanisms behind these synergistic interactions are to be expected because EGCG and caffeine act in concert along different control points underlying NE-induced thermogenesis. EGCG inhibits the enzyme catechol-O-methyltransferase that degrades NE within the synaptic cleft (Borchardt R T, Huber, J A, J Med Chem 1975; 18:120-2), whereas caffeine inhibits primarily the phosphodiesterase enzyme complex that degrades cyclic AMP, the intracellular secondary messenger for NE-mediated thermogenesis. The result is that two feedback inhibition pathways along the pathway of NE-activated thermogenesis have been removed. One would therefore expect the combination of EGCG and caffeine to be more effective than either compound alone in potentiating thermogenesis under sympathetic neural control.

US publication no. 20020192308 discloses an appetite suppressant comprising green tea; green tea leaf extract; and a chromium additive. US publication no. 20030143287 discloses a nutritional supplement for overweight and obese individuals, comprising a low-glycemic-index carbohydrate source, a source of protein and a source of fat; wherein the amounts of carbohydrate, protein and fat are sufficient for use in individuals to aid in the management of weight loss. US publication no. 20030162725 describes a pharmaceutical composition comprising an effective amount of a compound which enhances serotonin-mediated neurotransmission, or a pharmaceutically acceptable salt thereof, wherein said compound is selected from the group consisting of precursors of serotonin, pro-drugs of serotonin, or an intermediate in the biosynthesis of serotonin and a compound that promotes thermogenesis, wherein said compound is selected from the group consisting of epigallocatechin gallate or derivatives thereof. U.S. Pat. No. 6,565,896 discloses a cholesterol treatment composition comprising an effective amount of: Green Tea extract comprising standardized 98% polyphenols, 80% catechins; 45% EGCC; Gamma Oryzanol; Gugulipids; Beta Sitosterol; Artichoke extract standardized for 5% cynarine; Grape Seed extract comprising by weight 54% proanthocyanidin dimer, 13% proanthocyanidin trimer, 7% proanthocyanidin tetramer, and 6% monomer; Chromium; Pantethine; and Policosanol. US publication no. 20050256178 discloses a composition comprising biotin in an amount sufficient to administer to a subject a daily dosage of 0.01 mg per kg body weight to about 3 mg per kg body weight and at least one additional component selected from the group consisting of pantethine or a metabolite thereof, EGCG, phytanic acid, lipoic acid and policosanol.

US publication no. 20060078627 describes a composition for treatment of obesity or generally aiding weight loss, comprising: L-phenylalanine, caffeine, and one or more of the group of all forms of 5-hydroxytryptophan and L-tryptophan, all from either natural or synthetic sources. US publication no. 20060045913 describes a bi-layer tablet for the treatment of conditions associated with serotonin deficiencies in the nervous system characterized by the fact that at least one layer contains tryptophan and/or its metabolites, one of said layers under physiological conditions being a fast layer which possesses a rapid release rate and the other layer having a retarded release rate. US publication no. 20060078627 discloses a nutritional composition which promotes fast weight loss, burns calories, increases thermogenesis, supports energy metabolism and/or suppresses appetite in individuals, the nutritional composition comprising *Garcinia cambogia* extract, *Gymnema sylvestre* leaf extract, and green tea leaf extract. PCT publication no. WO2004041257 describes a composition for the treatment or prevention of type 2 diabetes in those individuals with pre-diabetes, or impaired glucose tolerance (IGT) or obesity comprising at least two components selected from EGCG, pantethine or a metabolite thereof, phytanic acid, lipoic acid, policosanol and coenzyme Q. U.S. Pat. No. 6,383,482 discloses a weight loss composition comprising effective amounts of: green tea extract; hydroxycitric acid; 5-hydroxytryptophan; glucomannan; chromium picolinate; and *Lactobacillus acidophilus*.

Overweight and obesity are associated with other chronic diseases such as type 2 diabetes mellitus, hypertension, coronary heart diseases and dyslipidemia, gallstones and cholecystectomy, osteoarthritis, cancer (of the breast, colon, endometrial, prostate, and gallbladder), and sleep apnea. It is estimated that there are around 32500 deaths annually that are attributable to obesity. The key to reducing the severity of the diseases is to lose weight effectively. Besides dietary manipulation, pharmacological management and in extreme cases, surgery, are sanctioned adjunctive therapies to treat overweight and obese patients (Expert Panel, National Institute of Health, Heart, Lung, and Blood Institute, 1-42 (June 1998); Bray, G. A., Contemporary Diagnosis and Management of Obesity, 246-273 (1998)). Drugs have side effects, and surgery, although effective is a drastic measure and reserved for morbidly obese. The present invention preferably provides anti-obesity compositions and method of manufacturing such novel compositions, which promote fast weight loss, burns calories, increase thermogenesis, support energy metabolism and/or suppress appetite in individuals. The compositions of the present invention comprise preferably natural product(s) as active agent(s) and are highly safe and effective, besides being economical to manufacture.

SUMMARY OF THE INVENTION

It is an objective of the present invention to provide novel compositions comprising a combination of at least one higher primary aliphatic alcohol(s) preferably selected from those having 18 to 40 carbon atoms or mixtures thereof and at least one source of 5-hydroxytryptophan (5-HTP) as active agents, either alone or in combination with other active agent(s), and optionally one or more excipient(s).

It is also an objective of the present invention to provide novel compositions comprising combination of at least one higher primary aliphatic alcohol(s) preferably selected from those having 18 to 40 carbon atoms or mixtures thereof, at least one source of 5-hydroxytryptophan (5-HTP) additionally comprising a source of caffeine and/or catechin-polyphenol and/or epigallocatechin gallate as active agents, either alone or in combination with other active agent(s), optionally with one or more excipient(s).

It is a further objective of the present invention to provide novel compositions comprising combination of at least one higher primary aliphatic alcohol(s) preferably selected from those having 18 to 40 carbon atoms or mixtures thereof, an extract of *Griffonia simplicifolia* comprising 5-hydroxytryptophan (5-HTP), an extract of Green tea comprising caffeine and/or catechin-polyphenol and/or epigallocatechin gallate as active agents, optionally with one or more excipient(s).

It is another preferred objective of the present invention to provide novel compositions for the management of obesity and associated disorders.

It is also an objective of the present invention to provide process for preparing or obtaining higher primary aliphatic alcohol(s), extract of *Griffonia simplicifolia* and extract of Green tea.

It is a further objective of the present invention to provide process for the preparation of such novel composition, which comprises of the following steps:
i) mixing higher primary aliphatic alcohol(s) with an extract of *Griffonia simplicifolia*,
ii) optionally adding an extract of Green tea,
iii) optionally adding one or more excipient(s), and
iv) formulation of the mixture into a suitable dosage form.

It is another objective of the present invention to provide a weight management kit for the management including prophylaxis, amelioration and/or treatment of obesity and associated disorders.

Yet another objective of the present invention is to provide method of using such novel compositions for the management of obesity and associated disorders which comprises administering to a subject in need thereof an effective amount of the composition.

The compositions of the present invention are useful as a pharmaceutical or as a dietary supplement. The compositions of the present invention are also highly effective and safe, and are economical to manufacture.

DETAILED DESCRIPTION OF THE INVENTION

The present invention provides novel compositions comprising a combination of at least one higher primary aliphatic alcohol(s) preferably selected from those having 18 to 40 carbon atoms or mixtures thereof and at least one source of 5-hydroxytryptophan (5-HTP) as active agent, either alone or in combination with other active agent(s), and optionally with one or more excipient(s). The compositions of the present invention are useful as a pharmaceutical or as a dietary supplement.

In an embodiment, the present invention provides novel compositions comprising combination of at least one higher primary aliphatic alcohol(s) preferably selected from those having 18 to 40 carbon atoms or mixtures thereof and at least one source of 5-hydroxytryptophan (5-HTP), additionally comprising a source of caffeine and/or catechin-polyphenol and/or epigallocatechin gallate as active agents, either alone or in combination with other active agent(s), optionally with one or more excipient(s).

In an embodiment, the present invention provides novel compositions comprising combination of at least one higher primary aliphatic alcohol(s) preferably selected from those having 18 to 40 carbon atoms or mixtures thereof, at least one source of caffeine and/or catechin-polyphenol and/or epigallocatechin gallate as active agents, optionally with one or more excipient(s).

In an embodiment, the present invention provides novel compositions comprising combination of at least one higher primary aliphatic alcohol(s) preferably selected from those having 18 to 40 carbon atoms or mixtures thereof, an extract of *Griffonia simplicifolia* comprising 5-hydroxytryptophan (5-HTP), an extract of Green tea comprising caffeine and/or catechin-polyphenol and/or epigallocatechin gallate, optionally with one or more excipient(s).

In a preferred embodiment of the present invention, novel compositions comprises about 0.1 mg to about 100 mg of higher primary aliphatic alcohol(s), about 0.5 mg to about 5 g of an extract of *Griffonia simplicifolia* and optionally about 0.5 mg to about 6 g an extract of Green tea. In a preferred embodiment, the compositions of the present invention are useful for the management of obesity and associated disorders. In another embodiment, the present invention provides novel compositions, which promotes fast weight loss, burns calories, increases thermogenesis, supports energy metabolism and/or suppresses appetites in individuals.

In an embodiment, the present invention provides process for preparing or obtaining the higher primary aliphatic alcohol(s), extract of *Griffonia simplicifolia* and extract of Green tea.

In an embodiment of the present invention is provided a process for the preparation of an extract comprising a mixture of higher primary aliphatic alcohol(s) along with source of 5-hydroxytryptophan (5-HTP) as active agents, optionally along with a source of caffeine, catechin-polyphenol and/or epigallocatechin gallate, which comprises the following steps:

i) Mixing of higher primary aliphatic alcohol(s) or the source comprising higher primary aliphatic alcohol(s) and dried powdered plant or part(s) of plant comprising 5-hydroxytryptophan (5-HTP),
ii) Extraction of the mixture of step (i) with a polar solvent or mixtures thereof,
iii) Distillation of the extract to remove the solvent,
iv) Optionally, washing of the residue dissolved in aqueous solvent with a non-polar solvent or a polar solvent or mixtures thereof,
v) Optionally, distillation of the extract to remove the solvent to obtain the desired extract,
vi) Optionally, isolation of desired material from the non-polar solvent or polar solvent by extraction with dilute aqueous acid or basification of the aqueous layer and extraction by a medium polar solvent,
vii) Optionally, washing of the desired compound by water and recrystallization.

In another embodiment of the present invention, a process for the preparation of an extract comprising a mixture of higher primary aliphatic alcohol(s) along with source of 5-hydroxytryptophan (5-HTP) as active agents either alone or in combination with other active agent(s), optionally a source of caffeine, catechin-polyphenol and/or epigallocatechin gallate comprises following steps:

i) Extraction of the dried and powdered plant or part(s) of plant comprising 5-hydroxytryptophan (5-HTP) with a polar solvent or mixtures thereof,
ii) Addition of higher primary aliphatic alcohol(s) such as octacosanol and mixing,
iii) Optionally adding an extract comprising caffeine, catechin-polyphenol and/or epigallocatechin gallate and mixing,
iv) Distillation of the mixture of step (ii) to remove the solvent,
v) Optionally, washing of the residue dissolved in aqueous solvent with a non-polar solvent or a polar solvent or mixtures thereof,
vi) Optionally, distillation of the extract to remove the solvent to obtain the desired extract,
vii) Optionally, isolation of desired material from the non-polar solvent or polar solvent by extraction with dilute aqueous acid or basification of the aqueous layer and extraction by a medium polar solvent,
viii) Optionally, washing of the desired compound by water and recrystallization.

In yet another embodiment of the present invention, a process for the preparation of an extract comprising 5-hydroxytryptophan (5-HTP), optionally along with a source of caffeine, catechin-polyphenol and/or epigallocatechin gallate is provided which comprises the following steps:

i) Extraction of dried and powdered part(s) of plants comprising 5-hydroxytryptophan (5-HTP) and optionally along with the dried and powdered part(s) of plant comprising caffeine, catechin-polyphenol and/or epigallocatechin gallate with a polar solvent or non-polar solvent or mixtures thereof,
ii) Distillation of the extract to remove the solvent,
iii) Optionally, washing of the residue dissolved in aqueous alkali with a medium polar solvent,
iv) Optionally, precipitation of the desired compound by acidification of the alkaline fraction and separation by filtration or centrifugation,
v) Optionally, washing of the desired compound by water and recrystallization.

In a further embodiment of the present invention, a process for the preparation of an extract of Green tea comprising at least caffeine, catechin-polyphenol and/or epigallocatechin gallate is provided, which comprises the following steps:

i) Extraction of dried and powdered plant or part(s) of the plant with a polar solvent or non-polar solvent or mixtures thereof,
ii) Distillation of the extract to remove the solvent,
iii) Optionally, washing of the residue dissolved in water with a non-polar solvent or mixtures thereof,
iv) Optionally, further extraction of the washed residue dissolved in water with a medium polar solvent,
v) Optionally, distillation of the extract to remove the solvent to obtain the desired extract,
vi) Optionally, isolation of caffeine from the non-polar solvent washing of step (iii) by extraction with dilute aqueous acid, basification of the aqueous layer and extraction by a medium polar solvent, and blending of the caffeine thus extracted with extract of step (v).

In a still further embodiment of the present invention, a process for the preparation of an extract of *Griffonia simplicifolia* is provided, which comprises the following steps:
i) Extraction of dried and powdered part(s) of the plant with a polar solvent or non-polar solvent or mixtures thereof,
ii) Distillation of the extract to remove the solvent,
iii) Optionally, washing of the residue dissolved in aqueous alkali with a medium polar solvent,
iv) Optionally, precipitation of the desired compound by acidification of the alkaline fraction and separation by filtration or centrifugation,
v) Optionally, washing of the desired compound by water and recrystallization.

The polar solvent used in the present invention is selected from but not limited to acetone, methanol, ethanol, isopropyl alcohol such as isopropanol, water, and the like used either alone or in combination thereof. The medium-polar solvent used in the present invention is selected from but not limited to chloroform, dichloromethane, dichloroethane, diethyl ether or mixtures thereof. The acid used in the present invention is selected from but not limited to hydrochloric acid, sulphuric acid, nitric acid, phosphoric acid, acetic acid, citric acid, tartaric acid and the like used either alone or in combination thereof. The alkali used for basification in the present invention is selected from but not limited to sodium hydroxide, sodium carbonate, potassium hydroxide, potassium carbonate, ammonium hydroxide, calcium hydroxide and the like used either alone or in combination thereof. The recrystallization solvent used in the present invention is selected from but not limited to ethanol, methanol, isopropanol, acetone, water, and the like used either alone or in combination thereof.

The higher primary aliphatic alcohol or a mixture of higher primary aliphatic alcohol(s) of the present invention can be obtained from a natural source such as preferably sugarcane wax, or synthesized. In a still further embodiment of the present invention, the process for the preparation of higher primary aliphatic alcohol(s) obtained from a natural source such as preferably sugarcane wax comprises the following steps:
i) isolating the wax containing the higher primary aliphatic alcohols,
ii) subjecting the wax to extraction with a liquid organic extractant in which primary aliphatic alcohols and other organic components are soluble,
iii) recovering said soluble mixture from said extractant,
iv) purifying the extract by repeated washing and crystallization,
v) optionally extracting a desired higher primary aliphatic alcohol,
vi) drying the extract comprising a mixture of higher primary aliphatic alcohols or a desired higher primary aliphatic alcohol at temperature preferably below 70° C. and making it into a powder form.

The wax is preferably isolated from a number of different sources, including sugarcane wax, beeswax, and rice bran wax, more preferably sugarcane wax. The liquid organic extractant of the present invention are selected from but not limited to a group comprising hexane, heptane, petroleum ether, chlorinated hydrocarbons, methanol, ethanol, isopropyl alcohol, ethyl acetate, acetone, ethyl methyl ketone, and the like, or mixtures thereof. In the said process, the soluble mixture from the said extractant is recovered by distillation, with or without the application of vacuum. The extract is purified preferably by repeated washing and crystallization methods. The solvents used for washing are selected from but not limited to hexane, heptane, petroleum ether, methanol, ethanol, isopropyl alcohol, ethyl acetate, acetone, ethyl methyl ketone, and the like, or mixtures thereof and the solvents for crystallization are selected from but not limited to hexane, heptane, petroleum ether, chlorinated hydrocarbons, methanol, ethanol, isopropyl alcohol, ethyl acetate, acetone, ethyl methyl ketone, toluene, and the like, or mixtures thereof. The extract is dried by subjecting it to hot air oven, or by a Fluid bed drier, preferably at temperature below 70° C.

In a preferred embodiment, the higher primary aliphatic alcohol(s) of the present invention is selected from but not limited to a group comprising 1-tetracosanol, 1-hexacosanol, 1-heptacosanol, 1-octacosanol, 1-nonacosanol, 1-tetratriacontanol, 1-triacontanol, 1-hexacontanol, eicosanol, 1-hexacosanol, 1-tetracosanol, 1-dotriacontanol, 1-tetracontanol, and the like or mixtures thereof. Preferably the mixture of higher primary aliphatic alcohols comprises 1-tetracosanol, 1-hexacosanol, 1-heptacosanol, 1-octacosanol, and 1-triacontanol, and the like. In a further embodiment, the present invention provides a composition comprising a mixture of higher primary aliphatic alcohol(s), wherein the mixture of higher primary aliphatic alcohol(s) is selected from a group comprising such alcohols having about 20 to about 39 carbon atoms preferably comprising 1-tetracosanol, 1-hexacosanol, 1-heptacosanol, 1-octacosanol, and 1-triacontanol.

In another embodiment of the present invention, the higher primary aliphatic alcohol or mixture of higher primary aliphatic alcohols is isolated from a number of different sources including plant sources such as sugarcane wax and rice bran wax, or animal sources or insects or honeycomb wax. The higher primary aliphatic alcohol(s) used in the preferred embodiment of the invention is preferably obtained from sugarcane wax. In a still further embodiment of the present invention, the composition comprises a mixture of higher primary aliphatic alcohols selected from a group comprising such alcohols having from about 18 to about 40 carbon atoms and other organic component(s) selected from resins and pigments, hydrocarbons, sterols, esters, ketones, aldehydes, and phenolic compounds preferably in the following amounts: 1-tetracosanol: 0.0-2.0%; 1-hexacosanol: 0.2-2.0%; 1-heptacosanol: 0.0-1.0%; 1-octacosanol: 30.0-40.0%; 1-triacontanol: 6.0-9.5%; Phytosterols: 0.1-1.0%; Resins and pigments: 5.0-10.0%; Hydrocarbons: 1.0-10.0%; Esters: 1.0-10.0%; Ketones and Aldehydes: 1.0-10.0% and Phenolic compounds: 0.0-5.0%.

The higher primary aliphatic alcohol or mixtures thereof useful in the present invention are obtained from a natural source such as a naturally occurring wax, a synthetic source or semi-synthetic source or a combination of such sources. The mixture of high-molecular weight aliphatic alcohols of the present invention occur naturally in wax form and are characterized by fatty alcohol chains ranging preferably from 20 to 39 carbon atoms in length. The major components of such mixture are the aliphatic alcohols such as 1-octacosanol and 1-triacontanol. The other component(s) includes one or more of 1-tetracosanol, 1-hexacosanol, 1-heptacosanol, 1-octacosanol, 1-nonacosanol, 1-tetratriacontanol, 1-triacontanol, 1-hexacontanol, eicosanol, 1-hexacosanol, 1-tetracosanol, 1-dotriacontanol, 1-tetracontanol, and the like. Other organic components such as resins, pigments, hydrocarbons, esters, ketones, aldehydes, phytosterols, phenolic compounds, and the like or mixtures thereof may be extracted along with the higher primary aliphatic alcohols from the same natural source or extracted from a different natural source and added to the composition or separately synthesized and then added to the composition. Such mixture of high-molecular weight aliphatic alcohols and other organic components of the present invention are preferably isolated from a number of different sources, including sugarcane wax, beeswax, and rice bran wax, more preferably sugarcane wax. It should be understood, however, that the invention is not limited in regard to the source and/or the number or amount of different higher primary aliphatic alcohol(s) used and/or other additional components used in the composition. In an embodiment, the mixture of high-molecular weight aliphatic alcohols useful in the present invention is policosanol.

In an embodiment of the present invention is provided a weight management kit for the management of obesity and associated disorders preferably comprising a combination of Starting Dose composition and Maintenance Dose composition. The weight management according to the present invention may be prophylaxis, amelioration and/or treatment. In an embodiment, the present invention provides a starting dose comprising at least one higher primary aliphatic alcohol(s) preferably selected from those having 18 to 40 carbon atoms or mixtures thereof, at least one source of 5-hydroxytryptophan (5-HTP) and at least a source of caffeine and/or catechin-polyphenol and/or epigallocatechin gallate, optionally with one or more excipient(s). In a further embodiment, the present invention provides a maintenance dose comprising at least one higher primary aliphatic alcohol(s) preferably selected from those having 18 to 40 carbon atoms or mixtures thereof, and at least a source of caffeine and/or catechin-polyphenol and/or epigallocatechin gallate, optionally with one or more excipient(s). In another embodiment, the present invention provides a weight management kit comprising starting composition and maintenance composition for the management of obesity and associated disorders, wherein the starting dose is administered for first 3 months and then maintenance dose is administered for another 3 months for the achievement of desired effects.

In another embodiment, the present invention provides a novel composition comprising combination of higher primary aliphatic alcohol(s), an extract of *Griffonia simplicifolia* and optionally an extract of Green tea as active agents, which additionally comprises one or more other active agent(s) that is a natural product or a pharmaceutical, wherein the other agent is selected from but not limited to a group comprising low-glycemic-index carbohydrate or protein or fat source or a mixture of such sources. The carbohydrate source can further provide a source of fiber and may be fructose, barley flakes, konjac mannan, psyllium and combinations thereof. The protein source is of a high biological value and is selected from but not limited to a group comprising whey protein concentrate, casein, soy, milk, egg and combinations of these. The fat is non-atherogenic oil, preferably one of the following namely canola, olive, soy, safflower, sunflower, corn and combinations of these; *Garcinia cambogia* (dried fruit and rind extract); *Gymnema sylvestre* leaf extract; N-olyl-phosphatidyl ethanolamine (NOPE)/EGCG blend (from standard green tea extract, *Camellia sinensis*); *Coleus forskohli, Citrus aurantium* extract; white tea dry leaf extract (*Camellia sinensis*); oolong tea dry leaf extract (*Camellia sinensis*); chromium polynicotinate; elemental chromium; *Rhodiola rosea* root extract; *Sida cordifolia* Extract; *Cassia Nomane* (whole plant) Hoodia 12:1 Extract (Cactus) Yohimbe 8% Extract (bark) Naringen (fruit); enriched soy phospholipid; *Withania somnifera* root extract; Mahuang herb extract; *Panax ginseng* root extract; *Atractylodes rhizome* (*Atractylodes macrocephale*), Baical skullcap root (*Scutellaria baicalensis*), Reishi mushroom (*Ganoderma lucidum*), Licorice root (*Glycyrrhiza uralensis*), Terra alba, Da huang root (*Rheum palmatum*), Mirabilite, Bladderwrack kelp (*Fucus vesiculosus*), Field mint herb (*Mentha haplocalyx*), Forsythia fruit (*Gardenia jasminoids*), Ginger root (*Zingiber officinale*), Lovage root (*Ligusticum wallichlii*), Schizonepeta stem (*Schizonepeta tenufolia*), Siler root (*Ledebouriella divaricata*), Siberian ginseng root (*Eleutherococcus senticosus*); cinnamon bark extract (*Cinnamomum cassia*); banaba leaf powder (*Lagerstroemia speciosa*); Forsythia (fruit), Sage (leaf) Black cohosh (root), Chasteberry (fruit), Shisandra (herb), Chlorella, St. John's Wort (herb) biotin; pantethine; phytanic acid; lipoic acid; dietary fibers; lipase inhibiting drugs such as Orlistat, and Xenical, or lipid absorbing polysaccharides such as Chitosan, or alpha amylase inhibitors such as acarbose, voglibose, miglitol, emiglitate, camiglibose, salbostatin that reduce starch intake in humans and the like. The compositions of the present invention are useful as a pharmaceutical or as a dietary/nutritional supplement. Additionally, the composition comprises micronutrients, vitamins, minerals, beneficial herbs, emulsifiers, flavorings and other edible compounds.

In a further embodiment, the novel composition of the present invention is useful in the management of obesity and associated disorders. Such disorders include but are not limited to a group comprising type 2 diabetes mellitus, hypertension, atherosclerosis, congestive heart failure, arthritis, coronary heart diseases and dyslipidemia, gallstones and cholecystectomy, osteoarthritis, cancer (of the breast, colon, endometrial, prostate, and gallbladder), sleep apnea, conditions associated with serotonin deficiencies in the nervous system, or a combination of such associated disorders.

In a further embodiment, the present invention also comprises other pharmaceutically acceptable active agent(s) known to the art, for the management of obesity and other associated disorders, such as a non-steroidal anti-inflammatory drug, a muscle relaxant, an antigout agent, an immunosuppressant, a drug affecting bone mineralization, an angiotensin-converting enzyme inhibitor, an antiarrhythmic drug, an anticoagulant, an antiplatelet agent, an antidiabetic agent, a thrombolytic, a beta-adrenergic blocking drug, a centrally acting drug, a digitalis drug, a nitrate, a peripheral adrenergic antagonist, a vasodilator, an acne medication, an antipruritic agent, an anti-psoriasis agent an anti-eczema agent, a hypnotic, an anti-histamine, a PPAR-gamma antagonist, insulin, a fibrate, an HMG-CoA reductase inhibitor, a bile acid sequestrant, a cholesterol absorption inhibitor, nicotinic acid, or their salts, derivatives, analogs and metabolites, and any mixture thereof.

Clinical Study

A clinical study was conducted on human patients to evaluate the efficacy and tolerability of the therapy consisting administration of formulations comprising *Griffonia simplicifolia* Extract, Green tea Extract, and a mixture of higher primary aliphatic alcohols, which is Purified *Saccharum officinarum* Wax (also referred to as 'policosanol'). The study was conducted on 120 subjects (42 males and 78 females) with age ranges between 18 to 55 years. Methodology included two therapies, i.e. Initial therapy and Maintenance therapy, wherein Initial therapy included administration of two caplets daily, one morning caplet half an hour before breakfast comprising 350 mg of Green tea extract and 100 mg of *Griffonia simplicifolia* extract; one evening caplet half an hour before dinner comprising 350 mg of Green tea extract, 100 mg of *Griffonia simplicifolia* extract and 20 mg of Purified *Saccharum Officinarum* Wax for three months. The Maintenance therapy included two caplets daily, one morning caplet half an hour before breakfast comprising 350 mg of Green tea extract; one evening caplet half an hour before dinner comprising 350 mg of Green tea extract and 20 mg of Purified *Saccharum Officinarum* Wax for another three months. Various parameters related to obesity were studied and it was concluded that there was significant reduction in all the critical parameters such as waist-hip ratio, mean body weight, body mass index (BMI), Obesity Related Well Being Score (ORWELL-97), calorie and carbohydrate intake etc. The data is presented in table-1.

TABLE 1

Data for evaluating efficacy of management of obesity using a formulation comprising *Griffonia simplicifolia* Extract, Green Tea Extract, and a mixture of higher primary alcohols

| Parameters | Pre-treatment (n = 109) | | Post-treatment (n = 109) | | Change in Parameter | Change (%) |
|---|---|---|---|---|---|---|
| | Mean | S.E.M | Mean | S.E.M | | |
| Weight (kg) | 87.5 | 1.00 | 82.4 | 0.98 | 5.1 | 5.8 |
| Waist circumference (cm) | 73.8 | 2.53 | 66.3 | 2.67 | 2.3 | 6.8 |
| Hip circumference (cm) | 84.0 | 3.26 | 75.7 | 3.43 | 7.54 | 10.2 |
| Waist-Hip ratio | 1.16 | 0.26 | 0.90 | 0.01 | 8.21 | 9.8 |
| BMI (kg/m$^2$) | 34.08 | 0.28 | 31.71 | 0.29 | 0.26 | 22.4 |
| ORWELL-97 | 72.87 | 1.23 | 51.9 | 1.09 | 343.37 | 24.3 |
| Calorie intake (kcalories) | 1410.32 | 30.07 | 1066.95 | 20.40 | 33.37 | 15.9 |
| Carbohydrate intake (gm) | 210.01 | 4.40 | 176.64 | 3.65 | 20.97 | 28.8 |

In an embodiment of the present invention, the composition can be formulated for administration by any suitable route such as the oral, rectal, nasal, or parenteral administration route. In a further embodiment, the composition of the present invention is preferably in the form of solid dosage forms such as tablets, capsules, pellets, granules or the like, more preferably as granules and pellets. Pharmaceutical compositions suitable for oral administration can be presented in discrete units, such as capsules, cachets, lozenges, or tablets, each containing a predetermined amount of active ingredients of the present invention; as a powder or granules; as a solution or a suspension in an aqueous or non-aqueous liquid; or as an oil-in-water or water-in-oil emulsion. Compressed tablets can be prepared by compressing, in a suitable machine, the material in a free-flowing form, such as a powder or granules optionally mixed with a binder, lubricant, inert diluent and/or surface active/dispersing agent(s). Molded tablets can be made, for example, by molding the powdered compound in a suitable machine. In a preferred embodiment, the solid oral dosage form compositions possess good bioavailability comprising one or more alkaline substance but devoid of any surfactants. In another preferred embodiment, the solid oral dosage form composition preferably as capsule is formulated as SMEDDS. Liquid dosage forms for oral administration can include pharmaceutically acceptable emulsions, solutions, suspensions, syrups, and elixirs containing inert diluents commonly used in the art, such as water. Such compositions may also comprise excipients such as wetting agents, emulsifying and suspending agents, and sweetening, flavoring, and perfuming agents. Pharmaceutical compositions suitable for buccal or sublingual administration include lozenges comprising a compound of the present invention in a flavored base, usually sucrose, and acacia or tragacanth, and pastilles comprising the drugs in an inert base such as gelatin and glycerin or sucrose and acacia.

In an embodiment of the present invention, the novel pharmaceutical composition useful in the management of obesity and associated disorders that can be combined with pharmaceutically acceptable excipients to produce a dosage form to be administered varies depending upon the host treated and the particular mode of administration. The pharmaceutically acceptable excipients that can be used for preparation of such compositions are selected from but not limited to diluents, disintegrants, binders, fillers, bulking agents, anti-adherants, anti-oxidants, buffering agents, colorants, flavoring agents, coating agents, plasticizers, organic solvents, stabilizers, preservatives, lubricants, glidants, chelating agents, and the like known to the art used either alone or in combination thereof.

In an embodiment, the filler(s) used in the present invention is selected from but not limited to a group comprising lactose, mannitol, sorbitol, starch, microcrystalline cellulose, xylitol, fructose, sucrose, dextrose, dicalcium phosphate, calcium sulphate and the like or mixtures thereof. The disintegrants used in the present invention include but not limited to starch or its derivatives, partially pregelatinized maize starch, croscarmellose sodium, sodium starch glycollate, and the like used either alone or in combination thereof. The lubricants used in the present invention include but not limited to talc, magnesium stearate, calcium stearate, stearic acid, hydrogenated vegetable oil and the like used either alone or in combination thereof. The tablets may be coated with a material such as glyceryl monostearate, glyceryl distearate, cellulose acetate phthalate, hydroxypropylcellulose phthalate, polyvinylacetate phthalate, methylmethacrylate polymer, a polymer mixture such as Eudragit®, a cellulose derivative, zein, wax or similar material, or any other dissolvable coat, to delay absorption in the gastrointestinal tract. Capsules for oral use include hard gelatin capsules in which the components are mixed with a solid diluent or soft gelatin capsules wherein the fill material exists as aqueous or hydroalcoholic or oily systems. The controlled release dosage form may be in the form of tablets, mini-tablets, capsules, pellets, granules, patches, powders and other dosage forms suitable for oral administration. In a preferred embodiment, the composition of the present invention is in the form of tablets. The tablets can be prepared by either direct compression, dry compression (slugging) or by granulation. In a preferred embodiment of the present invention, the oral composition is prepared by direct compression or compaction granulation. The composition prepared by granulation technique is either aqueous or non-aqueous. The non-aqueous solvent used is selected from a group comprising ethanol, isopropyl alcohol or methylene chloride. In an embodiment, the compositions of the present invention are in the form of compacted tablets/minitablets, compressed tablets/minitablets, or moulded tablets/minitablets prepared by extrusion or film cast technique, and the like. The tablets may be optionally coated with a nonfunctional coating to form a nonfunctional layer. The tablet/minitablets may be optionally filed into capsules.

In a further embodiment of the present invention is provided a process for the preparation of such novel composition which comprises the following steps:

i) mixing the higher primary aliphatic alcohol(s) with an extract of *Griffonia simplicifolia*,
ii) optionally adding an extract of Green tea and mixing,
iii) optionally adding one or more excipient(s), and
iv) formulation of the mixture into a suitable dosage form.

In an embodiment, the present invention provides a composition comprising mixture of higher primary aliphatic alcohol(s) along with source of 5-hydroxytryptophan (5-HTP) either alone or in combination with other active agent(s), optionally a source of caffeine and/or catechin-polyphenol and/or epigallocatechin gallate along with an additional composition that helps in absorbing the fats of the body (also referred to as 'Fat-absorption composition') for the management of obesity and associated disorders.

In another embodiment, the present invention provides a pharmaceutical or nutritional kit comprising a 'Fat-absorption composition'; a composition comprising a mixture of higher primary aliphatic alcohol(s) along with source of 5-hydroxytryptophan (5-HTP) either alone or in combination with other active agent(s) and optionally a source of caffeine, catechin-polyphenol and epigallocatechin gallate; and a nutritional supplement drink. The 'Fat-absorption composition' comprises components which can absorb, metabolize or assist in metabolizing or removing excess fats from the body such as chitosan, vitamins, and the like or mixtures thereof. The nutritional supplements are generally recommended to cope up with the conditions related to the nutritional deficiencies due to intake of low calorie diet or due to the less diet intake. Such supplements included one or more components selected from but not limited to a group comprising of vitamins such as vitamin A, vitamin E, thiamine, niacin, pyridoxine, cyanocobalamin and the like; minerals such as calcium, iron, copper, molybdenum, selenium and the like; proteins such as soya protein and the like; curcumin; carbohydrates such as guar gum and the like; fibres such as isabgol and the like, or any other component known to the art as a nutritional supplement. The pharmaceutical or nutritional kit of the present invention is preferably provided with instructions for the user indicating that the oral dosage units should be administered in accordance with the method as described in the instructions, wherein the instructions include administration of 2 unit dosage of 'Fat-absorption composition' taken 30 minutes before every meal accompanied with one or more glasses of water and administration of 1 unit dosage of composition as described in present invention thrice daily after meals and administration of 1 sachet of nutritional supplement drink stirred with a glass of water, skimmed milk or juice, whenever there is a craving for eating between the meals. The nutritional kit or dietary supplement particularly is intended to be useful prophylactically for obesity control.

In another embodiment of the present invention, the invention further provides use of such composition in the management of obesity and associated disorders. The present invention also provides a method of using such novel compositions for the management of obesity and associated disorders which comprises administering to a subject in need thereof an effective amount of the composition.

The examples given below serve to illustrate embodiments of the present invention. However they do not intend to limit the scope of present invention.

EXAMPLES

Preparation of Extract

Example-1

Extract-A 1 kg of dried and powdered *Griffonia simplicifolia* seeds were extracted with 5 L of 95% v/v aqueous ethanol by agitating at a temperature not more than 60° C. and filtered. The extraction was repeated 5 times and the pooled extract was distilled at reduced pressure to remove the solvent to get slurry. The slurry was dissolved in 1 L of 5% w/v sodium carbonate solution in water and filtered. The filtrate was extracted with 2 L of ethyl acetate four times. The alkaline fraction was separated and acidified with a 5% w/v aqueous solution of citric acid up to a pH of 4. The precipitated 5-HTP was separated by centrifugation and washed three times with 1 L water to remove the acid. The washed precipitates were recrystallized from 80% v/v ethanol.

Example-2

Extract-B 1 kg of dried Green tea leaf buds were extracted with 5 L of 60% v/v aqueous ethanol by agitating at a temperature not more than 60° C. and filtered. The extraction was repeated 5 times and the pooled extract was distilled at reduced pressure to remove the solvent to get slurry. The slurry was suspended in 1 L of water and extracted with 2 L of dichloromethane four times. The pooled dichloromethane extract was distilled to remove the solvent and set aside. The aqueous layer was further extracted with 2 L of ethyl acetate four times. The ethyl acetate extract was distilled to remove the solvent and set aside. The dichloromethane extract that was set aside, was partitioned between 1 L 2% aqueous citric acid and 1 L dichloromethane. The acidic layer was washed twice with 1 L dichloromethane. The acidic layer was basified with a saturated solution of sodium hydroxide up to a pH of 9. The basified layer was extracted with 2 L dichloromethane three times. The pooled dichloromethane extract was distilled to remove the solvent. This extract was mixed with the ethyl acetate extract set aside and dried.

Example-3

Extract-C 4 kg of air-dried Sugar mill Filter cake (or Press Mud) obtained as a byproduct during sugar manufacture from sugarcane was pulverized and extracted four times by boiling with 20 L of dichloroethane each time. The dichloroethane extract was filtered and the solvent was distilled off to get a dark green residue (400 g). The residue was extracted with 4 L of boiling methanol 3 times and the extract was filtered to remove the pitch while still hot (temperature above 50° C.). The filtered extract was distilled to remove methanol till a green residue (200 g) is obtained. The residue was dissolved in 2 L of boiling ethyl methyl ketone and set aside for crystallization. After complete crystallization the solvent is filtered, concentrated to half its volume by distillation and set aside for crystallization of the second crop. Both the crops were pooled and washed with cold hexane. The crystallization and washing procedures were repeated once more. The final washed crystals were dried under a current of air at a temperature not exceeding 70° C. The resultant creamish yellow lumps were pulverized to a fine powder (50 g).

Example-4

Extract-D

Beeswax obtained after extraction of honey from honeycomb was dried and pulverized and extracted four times by boiling with of ethyl alcohol each time. The alcoholic extract was filtered and the solvent was distilled off to get a residue. The residue was extracted with boiling methanol 3 times and the extract was filtered to remove the pitch while still hot (temperature above 50° C.). The filtered extract was distilled to remove methanol till a green residue is obtained. The residue was dissolved in boiling ethyl acetate and set aside for crystallization. After complete crystallization the solvent is filtered, concentrated to half its volume by distillation and set aside for crystallization of the second crop. Both the crops were pooled and washed with cold hexane. The crystallization and washing procedures were repeated once more. The final washed crystals were dried under a current of air at a temperature not exceeding 70° C. The resultant lumps were pulverized to a fine powder.

In the examples stated below describing compositions, the quantity of the active agent(s) stated may be varied based on the desired prophylactic or therapeutic effect and the type of composition.

Example-5

Capsule

| S. No. | Ingredient | mg/capsule |
| --- | --- | --- |
| 1 | Extract-A | 100.0 |
| 2 | Octacosanol | 20.0 |
| 3 | Mannitol | 72.0 |
| 4 | Talc | 3.0 |
| 5 | Sodium starch glycollate | 12.0 |
| 6 | Colloidal silicon dioxide | 12.0 |
| 7 | Macrocrystalline cellulose | 81.0 |

Procedure:
i) Extract-A, Octacosanol, Microcrystalline cellulose and Mannitol were sifted and mixed.
ii) Talc, sodium starch glycollate and colloidal silicon dioxide were passed through fine sieves individually and then mixed together.
iii) The materials of step (i) and (ii) were mixed together.
iv) The material of step (iii) was filled into empty hard gelatin capsules at an average fill weight of 300 mg±2%.
v) The filled capsules were packed in air-tight packages.

Example-6

Tablet

| S. No. | Ingredient | mg/tablet |
| --- | --- | --- |
| 1 | Extract-A | 100.0 |
| 2 | Extract-B | 350.0 |
| 3 | Extract-C | 20.0 |
| 4 | Lactose | 120.0 |
| 5 | Croscarmellose sodium | 10.0 |
| 6 | Talc | 4.0 |
| 7 | Colloidal silicon dioxide | 10.0 |

Procedure:
i) Extract-A, Extract-B, Extract-C, Lactose and Croscarmellose sodium were sifted and mixed together.
ii) The material of step (i) was compacted.
iii) The compacts of step (ii) were passed through sieve and mixed.
iv) Talc and Colloidal silicon dioxide were passed through fine sieve and mixed together.
v) The material of step (iii) was mixed with material of step (iv).
vi) The material of step (v) was compressed into tablets.

Example-7

Tablet

| S. No. | Ingredient | mg/tablet |
| --- | --- | --- |
| 1 | Extract-A | 120.0 |
| 2 | Extract-B | 300.0 |
| 3 | Extract-D | 40.0 |
| 4 | Biotin | 150.0 |
| 5 | Microcrystalline cellulose | 140.0 |
| 6 | Corn starch | 24.0 |
| 7 | Hydroxypropyl methylcellulose | 14.0 |
| 8 | Sodium stearyl fumarate | 4.0 |
| 9 | Colloidal silicon dioxide | 6.0 |

Procedure:
i) Extract-A, Extract-B, Extract-D, Biotin, Microcrystalline cellulose, Corn starch and Hydroxypropyl methylcellulose were sifted through 425 micron sieve.
ii) Material of step (i) was mixed in polygonal blender to obtain a uniform mixture.
iii) Sodium stearyl fumarate and Colloidal silicon dioxide were sifted through 250 micron sieve and mixed with the material of step (ii) in a blender.
iv) The material of step (iii) was compressed into tablets.

Example-8

Weight Management Kit

1) Starting Dose Composition

| S. No. | Ingredient | mg/tablet |
| --- | --- | --- |
| 1 | Extract B | 350.0 |
| 2 | Extract A | 100.0 |
| 3 | Extract C | 10.0 |
| 4 | Macrocrystalline cellulose | 216.0 |
| 5 | Starch | 68.0 |
| 6 | Sodium starch glycollate | 38.0 |
| 7 | Croscarmellose sodium | 19.0 |
| 8 | Colloidal silicon dioxide | 5.0 |
| 9 | Purified water | q.s. (lost in processing) |
| 10 | Starch | 67.0 |
| 11 | Sodium starch glycollate | 38.0 |
| 12 | Croscarmellose sodium | 19.0 |
| 13 | Colloidal silicon dioxide | 5.0 |
| 14 | Magnesium stearate | 5.0 |
| 15 | Talc | 10.0 |

Base Coating Composition:

| S. No. | Ingredient | mg/tablet |
| --- | --- | --- |
| 1 | Insta Moistshield Aqua II, White (Titanium dioxide) | 19.0 |
| 2 | Purified water | q.s. (lost in processing) |

Film Coating Composition:

| S. No. | Ingredient | mg/tablet |
| --- | --- | --- |
| 1 | Insta Moistshield Aqua II, Green (Titanium dioxide, Brilliant blue (lake) and Quinoline yellow (lake)) | 29.0 |
| 2 | Purified water | q.s. (lost in processing) |

Procedure:
i) Extract B, Extract A, Extract C, Microcrystalline Cellulose, Sodium Starch Glycollate, Croscarmellose Sodium, Colloidal Silicon Dioxide and Starch were sifted through sieve of mesh size 30 and mixed.
ii) Material of step (i) was granulated with purified water.
iii) Granules of step (ii) were passed through sieve of mesh size 18.
iv) Starch, Sodium Starch Glycolate, Crosscarmellose Sodium, Colloidal Silicon Dioxide, Magnesium Stearate and Talc were sifted through a sieve of mesh size 60 and mixed with the granules of step (iii) and compressed into tablets.
v) Dispersion of Insta Moistshield Aqua II, White in Purified Water was prepared.
vi) Dispersion of Insta Moistshield Aqua II, Green in Purified Water was prepared.
vii) Tablet of step (iv) was first coated with the dispersion of step (v) and then with the dispersion of step (vi).

2) Maintenance Dose Composition

| S. No. | Ingredient | mg/tablet |
| --- | --- | --- |
| 1 | Extract B | 350.0 |
| 2 | Extract C | 10.0 |
| 3 | Macrocrystalline cellulose | 145.0 |
| 4 | Starch | 39.0 |
| 5 | Sodium starch glycollate | 26.0 |
| 6 | Colloidal silicon dioxide | 3.0 |
| 7 | Purified water | q.s. (lost in processing) |
| 8 | Starch | 39.0 |
| 9 | Sodium starch glycollate | 26.0 |
| 10 | Colloidal silicon dioxide | 3.0 |
| 11 | Magnesium stearate | 3.0 |
| 12 | Talc | 6.0 |

Base Coating Composition:

| S. No. | Ingredient | mg/tablet |
| --- | --- | --- |
| 1 | Insta Moistshield Aqua II, White (Titanium dioxide) | 13.0 |
| 2 | Purified water | q.s. (lost in processing) |

Film Coating Composition:

| S. No. | Ingredient | mg/tablet |
| --- | --- | --- |
| 1) | Insta Moistshield Aqua II, Green (Titanium dioxide, Brilliant blue (lake) and Quinoline yellow (lake)) | 20.0 |
| 2) | Purified water | q.s. (lost in processing) |

Procedure:
i) Extract B, Extract C, Microcrystalline Cellulose, Sodium Starch Glycollate, Colloidal Silicon Dioxide and Starch were sifted through sieve of mesh size 30 and mixed.
ii) Material of step (i) was granulated with purified water.
iii) Granules of step (ii) were passed through sieve of mesh size 18.
iv) Starch, Sodium Starch Glycolate, Colloidal Silicon Dioxide, Magnesium Stearate and Talc were sifted through a sieve of mesh size 60 and mixed with the granules of step (iii) and compressed into tablets.
v) Dispersion of Insta Moistshield Aqua II, White in Purified Water was prepared.
vi) Dispersion of Insta Moistshield Aqua 11, Green in Purified Water was prepared.
vii) Tablet of step (iv) was first coated with the dispersion of step (v) and then with the dispersion of step (vi).

Both the compositions i.e. (1) and (2) are dispensed together as Weight management kit.

Example-9

Weight Management Kit

1) Fat Absorption Capsule

| S. No. | Ingredient | mg/tablet |
| --- | --- | --- |
| 1 | Chitosan | 120.0 |
| 2 | Vitamin C | 300.0 |
| 3 | Mannitol | 72.0 |
| 4 | Talc | 3.0 |
| 5 | Colloidal silicon dioxide | 12.0 |
| 6 | Macrocrystalline cellulose | 81.0 |

Procedure:
i) Chitosan, Vitamin C, microcrystalline cellulose and mannitol were sifted and mixed.
ii) Talc and colloidal silicon dioxide were passed through fine sieves individually and then mixed together.
iii) The materials of step (i) and (ii) were mixed together.
iv) The material of step (iii) was filled into empty hard gelatin capsules.

2) Obesity Management Tablet

| S. No. | Ingredient | mg/tablet |
| --- | --- | --- |
| 1 | Extract-A | 120.0 |
| 2 | Extract-C | 60.0 |
| 3 | Gymnema extract | 50.0 |
| 4 | Chromium polynicotinate | 0.001 |
| 5 | Dicalcium phosphate | 140.0 |
| 6 | Corn starch | 24.0 |
| 7 | Hydroxypropyl methylcellulose | 14.0 |
| 8 | Magnesium stearate | 4.0 |
| 9 | Colloidal silicon dioxide | 6.0 |

Procedure:
i) Extract-A, Extract-C, Gymnema extract, Chromium polynicotinate, Dicalcium phosphate, Corn starch and Hydroxypropyl methylcellulose were sifted through 425 micron sieve.
ii) Material of step (i) was mixed in polygonal blender to obtain a uniform mixture.
iii) Magnesium stearate and Colloidal silicon dioxide were sifted through 250 micron sieve and mixed with the material of step (ii) in a blender.
iv) The material of step (iii) was compressed into tablets.

3) Nutritional Supplement

| S. No. | Ingredient | Quantity/serving |
|---|---|---|
| 1 | Vitamin A | 500 μg |
| 2 | Vitamin E | 10 mg |
| 3 | Thiamine | 1.5 mg |
| 4 | Riboflavin | 0.8 mg |
| 5 | Niacin | 5 mg |
| 6 | Pyridoxine | 2 mg |
| 7 | Folic acid | 200 μg |
| 8 | Cyanocobalamin | 0.5 μg |
| 9 | Biotin | 100 μg |
| 10 | Cal. Pantothenate | 50 mg |
| 11 | Vitamin D | 5 μg |
| 12 | Calcium | 200 mg |
| 13 | Iron | 5 mg |
| 14 | Copper | 0.5 mg |
| 15 | Molybdenum | 10 mg |
| 16 | Selenium | 25 μg |
| 17 | Soya protein | 10 g |
| 18 | Curcumin | 200 mg |
| 19 | Isabgol | 1.5 g |
| 20 | Guar-gum | 0.5 g |
| 21 | Maltodextrin | 1.669 g |
| 22 | Sodium cyclamate | 0.115 g |
| 23 | Flavouring agent | 0.025 |
| 24 | Ethanol | q.s. (lost in processing) |
| 25 | Demineralized Water | q.s. (lost in processing) |

Procedure:

i) Vitamin A, Vitamin E, Thiamine, Riboflavin, Niacin, Pyridoxine, Folic acid, Cyanocobalamin, Biotin, Cal. Pantothenate, Vitamin D, Calcium, Iron, Copper, Molybdenum, Selenium, Soya protein, Curcumin, Isabgol, Guar-gum, Maltodextrin Sodium cyclamate and flavouring agent were mixed together and sieved.

ii) The mixture of step (i) is kneaded with a mixture of Ethanol and Demineralized water, granulated and dried to give a mixture.

All the three compositions i.e. (1), (2), and (3) are dispensed as Weight management kit.

Example-10

Film-Coated Tablet

Core Tablet Composition

| S. No. | Ingredient | Quantity/tablet |
|---|---|---|
| 1 | Extract-A | 100.0 mg |
| 2 | Extract-C | 20.0 mg |
| 3 | Chromium polynicotinate | 100.0 μg |
| 4 | Microcrystalline cellulose | 120.0 mg |
| 5 | Mannitol | 80.0 mg |
| 6 | Croscarmellose sodium | 10.0 mg |
| 7 | Lactose | 66.0 mg |
| 8 | Talc | 4.0 mg |
| 9 | Colloidal silicon dioxide | 10.0 mg |

Film Coating Composition

| S. No. | Ingredient | Quantity/tablet |
|---|---|---|
| 1 | Hydroxypropyl methylcellulose E-15 | 12.0 mg |
| 2 | Polyethylene glycol 400 (PEG 400) | 2.4 mg |
| 3 | Titanium dioxide | 0.25 mg |
| 4 | Isopropyl alcohol | q.s. (lost in processing) |
| 5 | Dichloromethane | q.s. (lost in processing) |

Procedure:

i) Extract-A, Extract-C, Chromium polynicotinate, microcrystalline cellulose, mannitol, croscarmellose sodium and lactose were sifted and mixed together.

ii) The material of step (i) was compacted.

iii) The compacts of step (ii) were passed through sieve and mixed.

iv) Talc, colloidal and silicon dioxide were passed through fine sieve and mixed together.

v) The material of step (iii) was mixed with material of step (iv).

vi) The material of step (v) was compressed into tablets.

vii) Hydroxypropyl methylcellulose was dispersed in a mixture of isopropyl alcohol and dichloromethane with continuous mixing in homogenizer.

viii) Polyethylene glycol 400 was added to the above solution of step (vii) and mixed.

ix) Titanium dioxide was passed through fine sieve and mixed with solution of step (viii).

x) The material of step (ix) was added to material of step (viii) and mixed for 30 minutes.

xi) The core tablets of step (vi) were charged into the coating pan and coated with the coating solution of step (x).

xii) The tablets were dried and packed in air-tight packages.

Example-11

Controlled Release Tablet

| S. No. | Ingredient | mg/tablet |
|---|---|---|
| 1) | Extract-A | 100.0 |
| 2) | Extract-B | 350.0 |
| 3) | Extract-C | 20.0 |
| 4) | Simvastatin | 13.5 |
| 5) | Lauryl macrogol glyceride | 13.50 |
| 6) | Microcrystalline cellulose | 12.00 |
| 7) | Chitosan | 42.00 |
| 8) | Hydroxyethyl cellulose | 21.00 |
| 9) | Polyvinylpyrrolidone (PVP K-90) | 7.50 |
| 10) | Isopropyl alcohol | q.s. (lost in processing) |
| 11) | Magnesium stearate | 2.00 |

Procedure:

i) Extract-A, Extract-B, Extract C, Simvastatin and Microcrystalline cellulose were mixed.

ii) Chitosan and Hydroxyethyl cellulose were mixed together separately.

iii) Blend of step (i) was mixed with blend of step (ii) and homogeneous mixture was formed.

iv) Polyvinylpyrrolidone was added to the homogeneous mixture of step (iii) and was sifted from #40 sieve.

v) Lauryl macrogol glyceride was dissolved in Isopropyl alcohol.

vi) Blend of step (iv) was granulated with the solution of step (v) and was passed through #30 sieve.

vii) The granules of step (vi) was dried and mixed with half quantity of Magnesium stearate.

viii) The blend of step (vii) was compacted and passed through the #30 sieve.

ix) The material of step (viii) was mixed with remaining quantity of Magnesium stearate and compressed into tablets.

We claim:

1. A composition comprising a combination of at least one higher primary aliphatic alcohol(s) selected from those having 18 to 40 carbon atoms or mixtures thereof and at least one source of 5-hydroxytryptophan (5-HTP) as active agents, either alone or in combination with other active agent(s), and optionally one or more excipient(s).

2. The composition according to claim 1, wherein the composition additionally comprises a source of caffeine, catechin-polyphenol or epigallocatechin gallate or a mixture of two or more thereof as the active agent(s).

3. The composition according to claim 1, wherein the composition additionally comprises one or more organic component(s) selected from resins and pigments, hydrocarbons, sterols, esters, ketones, aldehydes, and phenolic compounds.

4. The composition according to claim 3, wherein the composition comprises a mixture of higher primary aliphatic alcohols selected from a group comprising such alcohols having from about 18 to about 40 carbon atoms and other organic component(s) selected from resins and pigments, hydrocarbons, sterols, esters, ketones, aldehydes, and phenolic compounds preferably in the following amounts: 1-tetracosanol: 0.0-2.0%; 1-hexacosanol: 0.2-2.0%; 1-heptacosanol: 0.0-1.0%; 1-octacosanol: 30.0-40.0%; 1-triacontanol: 6.0-9.5%; phytosterols: 0.1-1.0%; resins and pigments:5.0-10.0%; hydrocarbons: 1.0-10.0%; esters: 1.0-10.0%; ketones and aldehydes: 1.0-10.0% and phenolic compounds: 0.0-5.0%.

5. The composition according to claim 1, wherein the source of 5-hydroxytryptophan (5-HTP) is an extract of *Griffonia simplicifolia*.

6. The composition according to claim 2, wherein the source of one or more of caffeine, catechin-polyphenol, and epigallocatechin gallate is an extract of Green tea.

7. The composition according to claim 2, wherein the composition comprises about 0.1 to about 100 mg of higher primary aliphatic alcohol(s), about 0.5 mg to about 5 g of an extract of *Griffonia simplicifolia* and about 0.5 mg to about 6 g of an extract of Green tea.

8. The composition according to claim 1, wherein the higher primary aliphatic alcohol(s) is selected from a group comprising 1-tetracosanol, 1-hexacosanol, 1-heptacosanol, 1-octacosanol, 1-nonacosanol, 1-tetratriacontanol, 1-triacontanol, 1-hexacontanol, eicosanol, 1-hexacosanol, 1-tetracosanol, 1-dotriacontanol, 1-tetracontanol, and the like or mixtures thereof.

9. The A composition according to claim 1, wherein the other active agent(s) is a non-steroidal anti-inflammatory drug, a muscle relaxant, an antigout agent, an immunosuppressant, a drug affecting bone mineralization, an angiotensin-converting enzyme inhibitor, an antiarrhythmic drug, an anticoagulant, an antiplatelet agent, an antidiabetic agent, a thrombolytic, a beta-adrenergic blocking drug, a centrally acting drug, a digitalis drug, a nitrate, a peripheral adrenergic antagonist, a vasodilator, an acne medication, an antipruritic agent, an anti-psoriasis agent, an anti-eczema agent, a hypnotic, an anti-histamine, a PPAR-gamma antagonist, insulin, a fibrate, an HMG-CoA reductase inhibitor, a bile acid sequestrant, a cholesterol absorption inhibitor, nicotinic acid or their salts, analogs and metabolites, and any mixture thereof.

10. The A composition according to claim 1, wherein the composition is administered for the management of obesity and associated disorders.

11. The A composition according to claim 1, wherein the composition is administered as a pharmaceutical or as a dietary/nutritional supplement.

12. A composition in the form of a kit which comprises a starting dose composition as claimed in claim 1, along with a maintenance dose composition, wherein the starting dose is administered for first 3 months and then maintenance dose is administered for another 3 months for the achievement of desired effects.

13. The A composition according to claim 12, wherein the Maintenance Dose composition comprises at least one higher primary aliphatic alcohol(s) selected from those having 18 to 40 carbon atoms or mixtures thereof, wherein preferably the higher primary aliphatic alcohol(s) is extracted from sugarcane wax and at least a source of caffeine and/or catechin-polyphenol and/or epigallocatechin gallate, optionally with one or more excipient(s).

14. A composition in the form of a kit which comprises a composition according to claim 1 along with a Fat-absorption composition comprising components which can absorb, metabolize or assist in metabolizing or removing excess fats from the body such as chitosan, vitamins, and the like or mixture thereof and a nutritional supplement drink.

15. A process of preparation of a pharmaceutical composition according to claim 1, which comprises the following steps:
   i) mixing the higher primary aliphatic alcohol(s) with an extract of *Griffonia simplicifolia*,
   ii) optionally adding an extract of Green tea and mixing,
   iii) optionally adding one or more excipient(s), and
   iv) formulating the mixture of step i), ii) or iii) into a suitable dosage form.

16. A method of treating a disorder comprising administering an effective amount of the composition according to claim 1, for the management of obesity and associated disorders.

17. A method of treating according to claim 12, for the management of obesity and associated disorders comprising administering to a subject a weight management kit comprising a combination of a starting dose composition and a maintenance dose composition, wherein the starting dose is administered for first 3 months and then maintenance dose is administered for another 3 months for the achievement of desired effects.

18. A method of treating according to claim 10 or 16, wherein the associated disorders are selected from a group comprising type 2 diabetes mellitus, hypertension, atherosclerosis, congestive heart failure, arthritis, coronary heart diseases and dyslipidemia, gallstones and cholecystectomy, osteoarthritis, breast cancer, colon cancer, endometrial cancer, prostate cancer, gallbladder cancer, sleep apnea, conditions associated with serotonin deficiencies in the nervous system, or a combination of such associated disorders.

* * * * *